US012458762B2

(12) United States Patent
Clasen

(10) Patent No.: US 12,458,762 B2
(45) Date of Patent: Nov. 4, 2025

(54) INTEGRATED ADHESIVE LINER AND NEEDLE SHIELD REMOVER FOR DRUG DELIVERY SYSTEM

(71) Applicant: Becton, Dickinson and Company, Franklin Lakes, NJ (US)

(72) Inventor: Eric Scott Clasen, Hillsborough, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 782 days.

(21) Appl. No.: 17/706,034

(22) Filed: Mar. 28, 2022

(65) Prior Publication Data

US 2022/0313925 A1 Oct. 6, 2022

Related U.S. Application Data

(60) Provisional application No. 63/169,589, filed on Apr. 1, 2021.

(51) Int. Cl.
*A61M 5/32* (2006.01)
*A61M 5/142* (2006.01)

(52) U.S. Cl.
CPC ...... *A61M 5/3204* (2013.01); *A61M 5/14248* (2013.01)

(58) Field of Classification Search
CPC ............ A61M 5/3204; A61M 5/14248; A61M 2005/14252; A61M 2005/14268; A61M 2005/1581
See application file for complete search history.

(56) References Cited

U.S. PATENT DOCUMENTS

| | | | | |
|---|---|---|---|---|
| 5,858,001 A * | 1/1999 | Tsals | ................. | A61M 5/14248 604/232 |
| 7,054,575 B1 * | 5/2006 | Michlin | ............. | G03G 15/0894 399/106 |
| 8,303,535 B2 | 11/2012 | Both et al. | | |

(Continued)

FOREIGN PATENT DOCUMENTS

| | | | |
|---|---|---|---|
| EP | 0989871 B1 | 9/2004 | |
| WO | 2013155153 A1 | 10/2013 | |

(Continued)

*Primary Examiner* — Yashita Sharma
*Assistant Examiner* — Lei Gonzalez
(74) *Attorney, Agent, or Firm* — The Webb Law Firm

(57) ABSTRACT

A drug delivery system includes a housing, a needle having a retracted position within the housing and an extended position outside of the housing, an adhesive pad element coupled to a bottom portion of the housing, the adhesive pad element including a primary adhesive layer and a removable liner, and a needle shield portion. The system also includes a needle shield remover having an elongated member configured to extend along the bottom portion of the housing in a first position and extend away from the bottom portion of the housing in a second position, a bottom surface portion of the elongated member being coupled to the removable liner proximate to an edge location of the adhesive pad element such that the removable liner is peeled away from the primary adhesive layer when the elongated member of the needle shield remover is moved from the first position to the second position.

15 Claims, 14 Drawing Sheets

(56) References Cited

U.S. PATENT DOCUMENTS

| | | | | |
|---|---|---|---|---|
| 8,961,469 | B2 * | 2/2015 | Sonderegger ..... | A61M 5/14244 604/257 |
| 9,427,529 | B2 * | 8/2016 | Cabiri ............... | A61M 5/14248 |
| 10,391,245 | B2 | 8/2019 | Cronenberg et al. | |
| 10,583,241 | B2 | 3/2020 | Wu et al. | |
| 11,364,336 | B2 | 6/2022 | Cronenberg | |
| 2016/0228652 | A1 | 8/2016 | Cabiri et al. | |
| 2018/0154079 | A1 * | 6/2018 | Anderson ......... | A61M 5/14248 |
| 2019/0060571 | A1 | 2/2019 | Cabiri et al. | |
| 2019/0381239 | A1 | 12/2019 | Cabiri et al. | |

FOREIGN PATENT DOCUMENTS

| | | | |
|---|---|---|---|
| WO | 2014179774 | A1 | 11/2014 |
| WO | 2015081337 | A2 | 6/2015 |

* cited by examiner

INTEGRATED ADHESIVE LINER AND NEEDLE SHIELD REMOVER FOR DRUG DELIVERY SYSTEM

CROSS-REFERENCE TO RELATED APPLICATION

This application claims priority to U.S. Provisional Application No. 63/169,589, entitled "Integrated Adhesive Liner and Needle Shield Remover for Drug Delivery System", filed Apr. 1, 2021, the entire disclosure of which is hereby incorporated by reference in its entirety.

BACKGROUND OF THE INVENTION

Field of the Disclosure

The present disclosure relates generally to an injector device and method for delivering a fluid into the body of a patient by injection.

Description of the Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism that can be triggered by the user. When the volume of fluid or drug to be administered is generally below a certain volume, such as 1 mL, an auto-injector is typically used, which typically has an injection time of about 10 to 15 seconds. When the volume of fluid or drug to be administered is above 1 mL, the injection time generally becomes longer, resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually injecting a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection needle. Such devices also typically include a valve or flow control mechanism to cause the liquid therapeutic preparation to begin to flow at the proper time and a triggering mechanism to initiate the injection.

In certain wearable injector devices, the device is coupled to the patient's skin via an adhesive pad, with the non-patient-facing side of the adhesive pad also being partially adhered to a bottom surface of the injector device. Prior to use, the patient-facing side of the adhesive pad is covered with a liner, and the liner must be removed in order to expose the adhesive surface of the adhesive pad for placement on the patient's skin. Additionally, a needle shield remover may be provided over both the adhesive pad and the liner at a substantially centralized location, with a portion of the needle shield remover passing through the liner, the adhesive pad, and an opening in the bottom surface of the injector device to a needle shield formed on an end thereof. The needle shield is configured to provide protection over the injection needle within the injection device prior to use, and also to prevent inadvertent initiation of the injection process.

In a wearable injector device such as that described above, the needle shield remover may include a grasping portion (e.g., a ring), which may be pivotable from a non-use to a use position via, e.g., a living hinge. Furthermore, a portion of the needle shield remover may be affixed to the liner via, e.g., a mechanical connection, an adhesive, etc. Thus, when the injector device is ready to be placed on the patient's skin, the grasping portion is pivoted to the use position and pulled in a direction substantially perpendicular to the bottom surface of the injector device. Such a pulling force on the grasping portion not only removes the needle shield, but also acts to remove the liner over the adhesive pad due to the connection between the needle shield remover and the liner, thereby preparing the injector device for placement on the patient's skin in a single step.

However, there are certain disadvantages to the existing correlation between removal of the needle shield and removal of the liner on the adhesive pad. Specifically, the needle shield remover is centrally positioned relative to the liner and adhesive pad. Thus, when the grasping portion of the needle shield remover is pulled to remove the needle shield, removal of the liner begins at a location proximate this central position on the adhesive pad. Such an "inside-out" removal of the liner necessitates that the liner be cut or perforated along certain portions thereof, known as a "kiss cut", which allows the liner to be removed via the needle shield remover in a spring-like or spiral fashion. However, providing these cuts or perforations in only the liner (and not the underlying adhesive pad) is complex and difficult to reliably achieve during manufacturing. Furthermore, junctions of the cuts or perforations in such a liner must be reinforced so as to prevent tearing due to impulse loading when the grasping portion is pulled and/or when the needle shield remover and needle shield exit the injector device. Additionally, peeling the liner in such a way may be awkward or confusing to the user, at it is far less conventional than beginning the peel/removal from an edge of a pad.

SUMMARY OF THE INVENTION

In one aspect of the present disclosure, a drug delivery system includes a housing having a top portion and a bottom portion, a needle having a retracted position within the housing and an extended position outside of the housing. The drug delivery system also includes an adhesive pad element coupled to the bottom portion of the housing, wherein the adhesive pad element includes a primary adhesive layer and a removable liner. The drug delivery system further includes a needle shield portion configured to at least partial cover the needle in the retracted position, and a needle shield remover coupled to the needle shield portion. The needle shield remover includes an elongated member configured to extend along the bottom portion of the housing in a first position and extend away from the bottom portion of the housing in a second position, a bottom surface portion of the elongated member being coupled to the removable liner proximate to an edge location of the adhesive pad element such that the removable liner is peeled away from the primary adhesive layer when the elongated member of the needle shield remover is moved from the first position to the second position.

In a further configuration of the drug delivery system, the needle shield remover further includes a grasping portion on a distal end of the elongated member. Optionally, the grasping portion includes a pull tab. The pull tab may be angled upwards relative to the bottom portion of the housing when the elongated member is in the first position. In a further configuration, the grasping portion includes a pull ring.

In other configurations, the needle shield remover further includes a hinge portion. In one aspect, the elongated member moves from the first position to the second position by pivoting about the hinge portion. Optionally, the bottom surface portion of the elongated member is coupled to the removable liner by an adhesive. The adhesive pad element further includes an extended portion extending below the bottom surface portion of the elongated member. In certain configurations, the shielding portion of the needle shield remover passes through the liner of the adhesive pad element, the primary adhesive layer of the adhesive pad element, and an opening formed in the housing to allow the needle to extend therethrough in the extended position.

In additional configurations, the adhesive pad element further includes an injector removal tab. Optionally, a peripheral portion of the adhesive pad element extends beyond a footprint of the housing. It is noted that the adhesive pad element may be formed of one or more flexible materials. In addition, the elongated member of the needle shield remover may be formed of a flexible material. The elongated member of the needle shield remover may lay substantially flat along the bottom portion of the housing when in the first position.

In accordance with another embodiment of the present invention, a method of preparing a wearable drug delivery system for use includes providing a drug delivery system having a housing having a top portion and a bottom portion, a needle having a retracted position within the housing and an extended position outside of the housing, and an adhesive pad element coupled to the bottom portion of the housing. The adhesive pad element may include a primary adhesive layer and a removable liner. The drug delivery system further includes a needle shield portion configured to at least partial cover the needle in the retracted position, and a needle shield remover coupled to the needle shield portion. The needle shield remover may include an elongated member having a grasping portion on a distal end thereof, the elongated member may be configured to extend along the bottom portion of the housing in a first position and extend away from the bottom portion of the housing in a second position. A bottom surface portion of the elongated member may be coupled to the removable liner proximate to an edge location of the adhesive pad element. The method further includes pivoting the elongated member from the first position towards the second position such that the removable liner is peeled away from the primary adhesive layer at the edge location of the adhesive pad element. In addition, the method further includes pulling the grasping portion of the needle shield remover to both remove the needle shield portion from the housing and remove the removable liner from the primary adhesive layer.

In certain configurations, pivoting the elongated member from the first position towards the second position includes pivoting the elongated member about a hinge portion of the needle shield remover. Optionally, the grasping portion of the needle shield remover includes a pull tab. The grasping portion of the needle shield remover may include a pull ring. In certain configurations, the edge location of the adhesive pad element is a front edge portion coupled to the bottom portion of the housing via an adhesive. The bottom surface portion of the elongated member may be coupled to the removable liner of the adhesive pad element at a location proximate to the front edge portion.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary aspects of the disclosure, and such exemplifications are not to be construed as limiting the scope of the disclosure in any manner.

DETAILED DESCRIPTION

Figure 1:
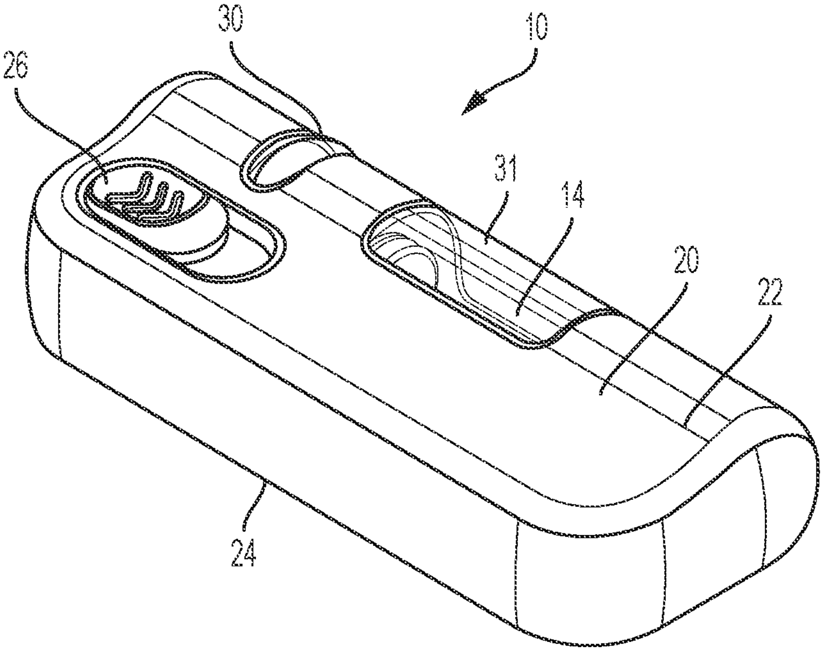
FIG. 1 is a perspective view of a drug delivery system according to one aspect of the present invention.
Figure 2:
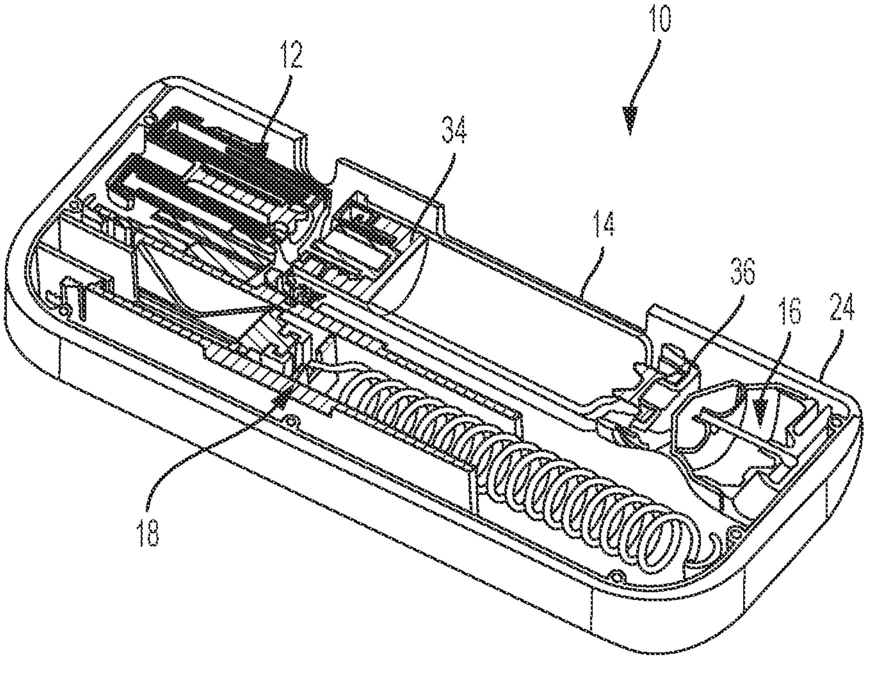
FIG. 2 is a perspective, cross-sectional view of the drug delivery system of FIG. 1 according to one aspect of the present invention.
Figure 3:
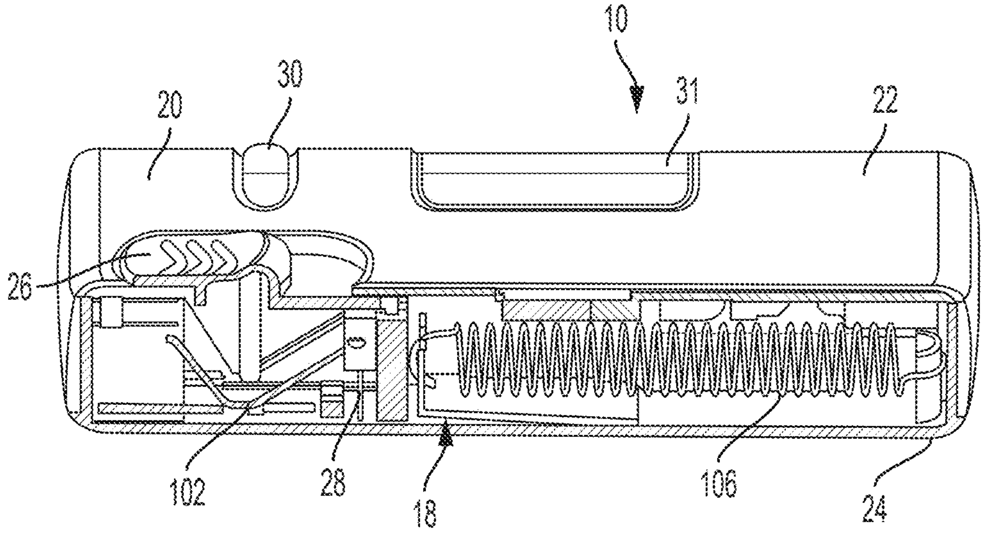
FIG. 3 is a front, cross-sectional view of the drug delivery system of FIG. 1 according to one aspect of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-16, a drug delivery system 10 according to one aspect of the present invention includes a drive assembly 12, a container 14, a valve assembly 16, and a needle actuator assembly 18. The drive assembly 12, the container 14, the valve assembly 16, and the needle actuator assembly 18 are at least partially positioned within a housing 20. The housing 20 includes a top portion 22 and a bottom portion 24, although other suitable arrangements for the housing 20 may be utilized. In one aspect, the drug delivery system 10 is an injector device configured to be worn or secured to a user and to deliver a predetermined dose of a medicament provided within the container 14 via injection into the user. The system 10 may be utilized to deliver a "bolus injection" where a medicament is delivered within a set time period. The medicament may be delivered over a time period of up to 45 minutes, although other suitable injection amounts and durations may be utilized. A bolus administration or delivery can be carried out with rate controlling or have no specific rate controlling. The system 10 may deliver the medicament at a fixed pressure to the user with the rate being variable. The general operation of the system 10 is described below in reference to FIGS. 1-16.

Referring again to FIGS. 1-16, the system 10 is configured to operate through the engagement of an actuation button 26 by a user, which results in a needle 28 of the needle assembly 18 piercing the skin of a user, the actuation of the drive assembly 12 to place the needle 28 in fluid communication with the container 14 and to expel fluid or medicament from the container 14, and the withdrawal of the needle 28 after injection of the medicament is complete. The general operation of a drug delivery system is shown and described in International Publication Nos. 2013/155153 and 2014/179774, which are hereby incorporated by reference in their entirety. The housing 20 of the system 10 includes an indicator window 30 for viewing an indicator arrangement 32 configured to provide an indication to a user on the status of the system 10 and a container window 31 for viewing the container 14. The indicator window 30 may be a magnifying lens for providing a clear view of the indicator arrangement 32. The indicator arrangement 32 moves along with the needle actuator assembly 18 during use of the system 10 to indicate a pre-use status, use status, and post-use status of the system 10. The indicator arrangement 32 provides visual indicia regarding the status, although other suitable indicia, such an auditory or tactile, may be provided as an alternative or additional indicia.

Figure 4:
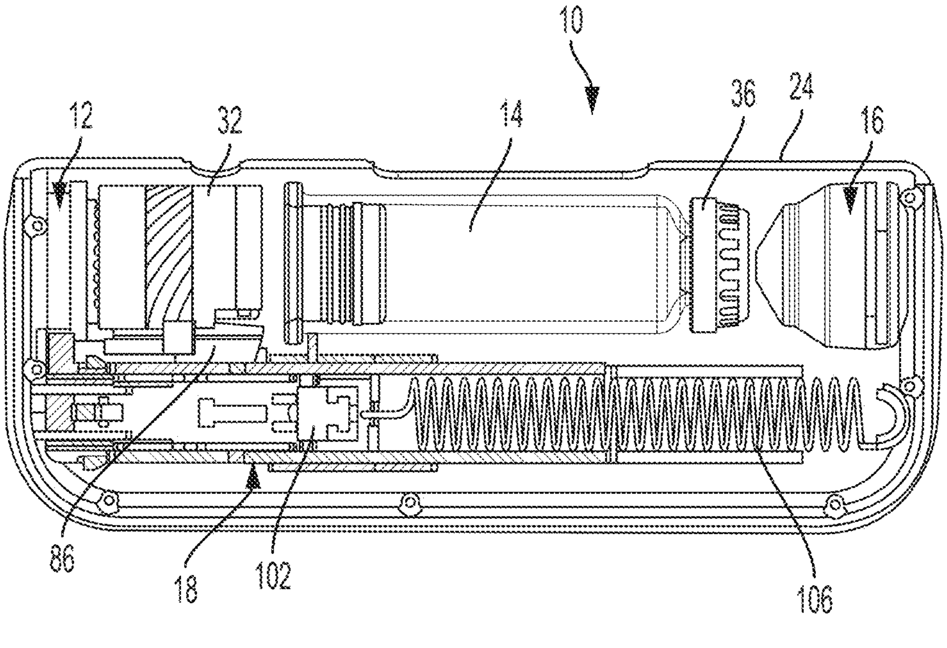
FIG. 4 is a top view of the drug delivery system of FIG. 1 according to one aspect of the present invention, showing a top portion of the housing removed and the drug delivery system in a pre-use position.
Figure 5:
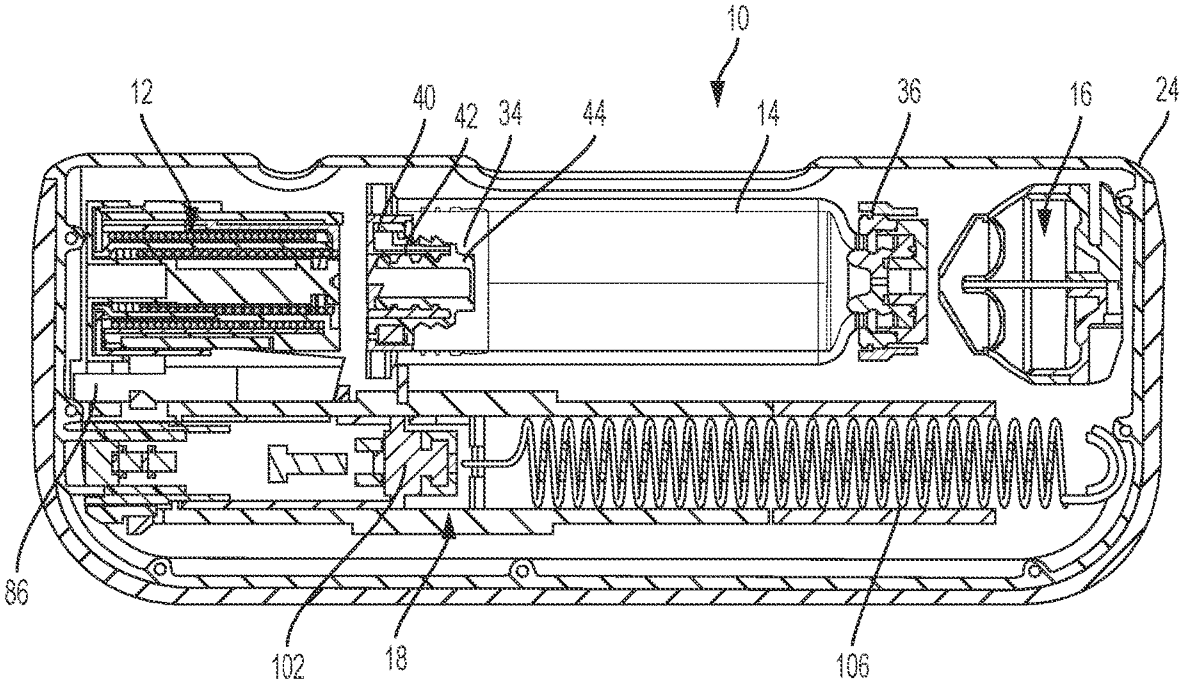
FIG. 5 is a top, cross-sectional view of the drug delivery system of FIG. 1 according to one aspect of the present invention, showing the drug delivery system in a pre-use position.
Figure 6:
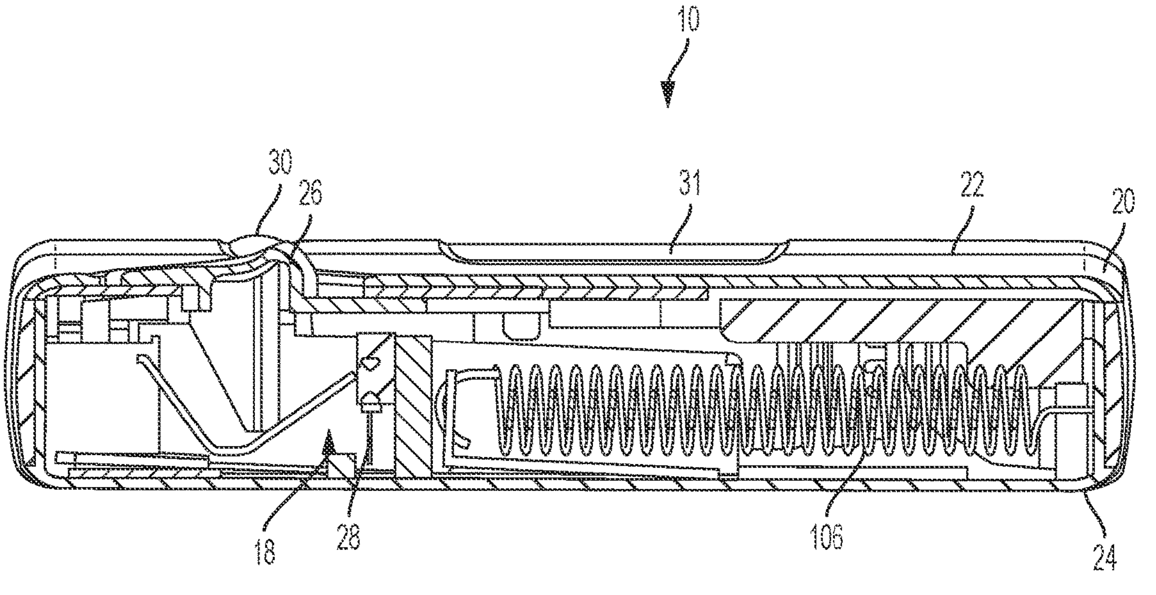
FIG. 6 is a front, cross-sectional view of the drug delivery system of FIG. 1 according to one aspect of the present invention, showing the drug delivery system in a pre-use position.
Figure 7:
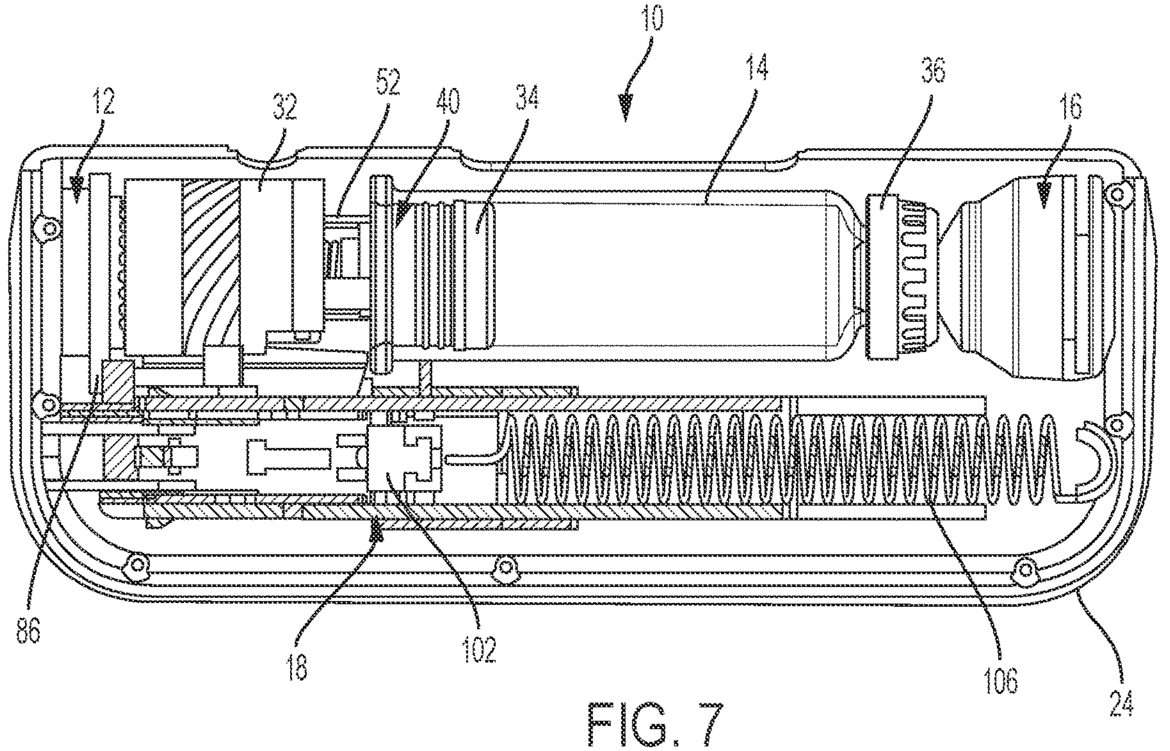
FIG. 7 is a top view of the drug delivery system of FIG. 1 according to one aspect of the present invention, showing a top portion of the housing removed and the drug delivery system in an initial actuation position.
Figure 8:
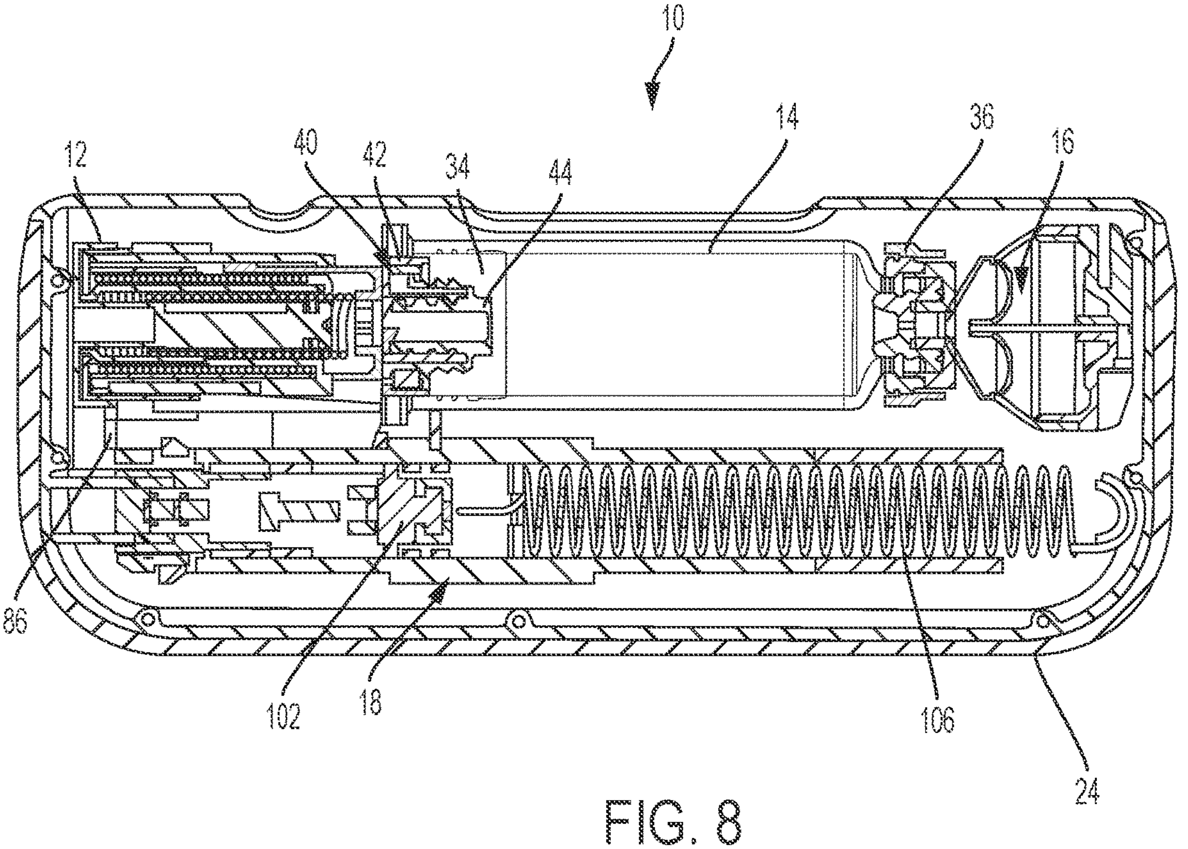
FIG. 8 is a top, cross-sectional view of the drug delivery system of FIG. 1 according to one aspect of the present invention, showing the drug delivery system in an initial actuation position.
Figure 9:
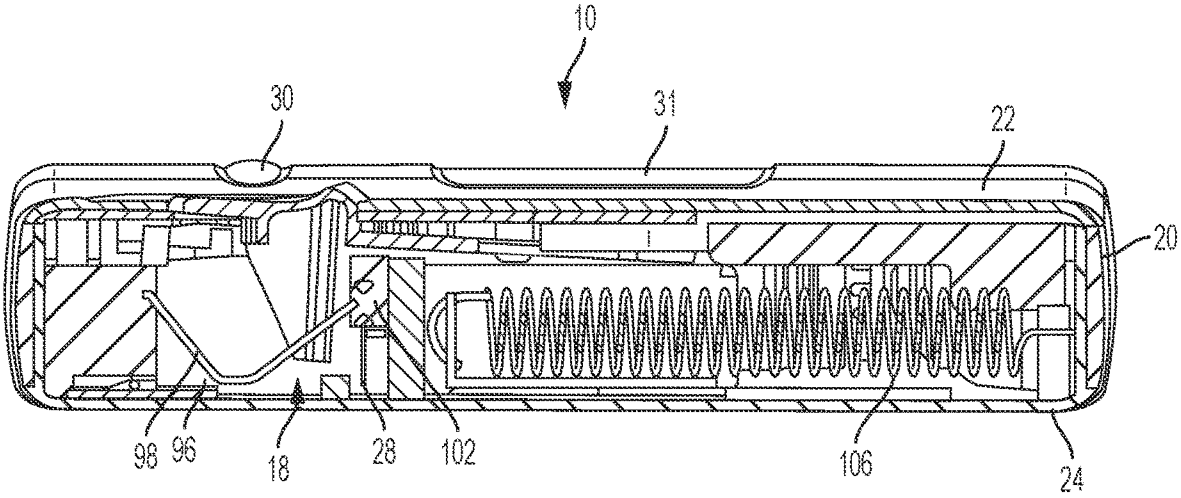
FIG. 9 is a front, cross-sectional view of the drug delivery system of FIG. 1 according to one aspect of the present invention, showing the drug delivery system in an initial actuation position.

Referring to FIGS. 4-6, during a pre-use position of the system 10, the container 14 is spaced from the drive assembly 12 and the valve assembly 16 and the needle 28 is in a retracted position. During the initial actuation of the system 10, as shown in FIGS. 7-9, the drive assembly 12 engages the container 14 to move the container 14 toward the valve assembly 16, which is configured to pierce a closure 36 of the container 14 and place the medicament within the container 14 in fluid communication with the needle 28 via a tube (not shown) or other suitable arrangement. The drive assembly 12 is configured to engage a stopper 34 of the container 14, which will initially move the entire container 14 into engagement with the valve assembly 16 due to the incompressibility of the fluid or medicament within the container 14. The initial actuation of the system 10 is caused by engagement of the actuation button 26 by a user, which releases the needle actuator assembly 18 and the drive assembly 12 as discussed below in more detail. During the initial actuation, the needle 28 is still in the retracted position and about to move to the extended position to inject the user of the system 10.

Figure 10:
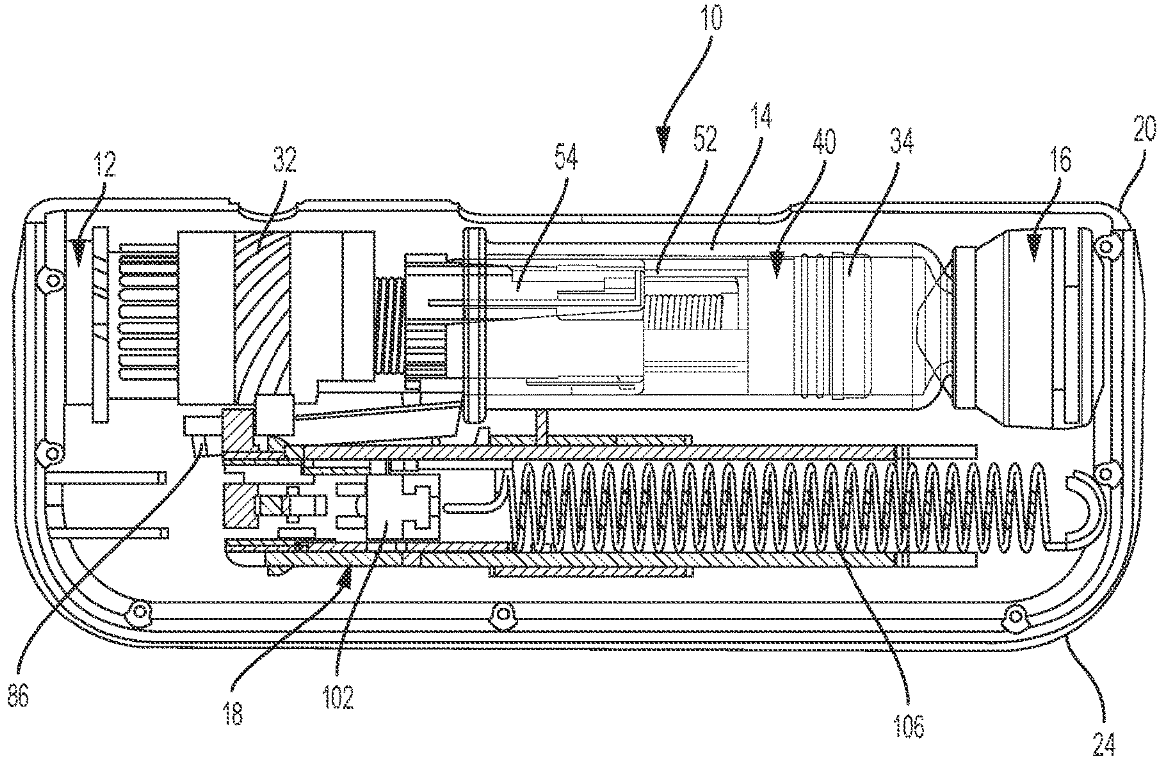
FIG. 10 is a top view of the drug delivery system of FIG. 1 according to one aspect of the present invention, showing a top portion of the housing removed and the drug delivery system in a use position.
Figure 11:
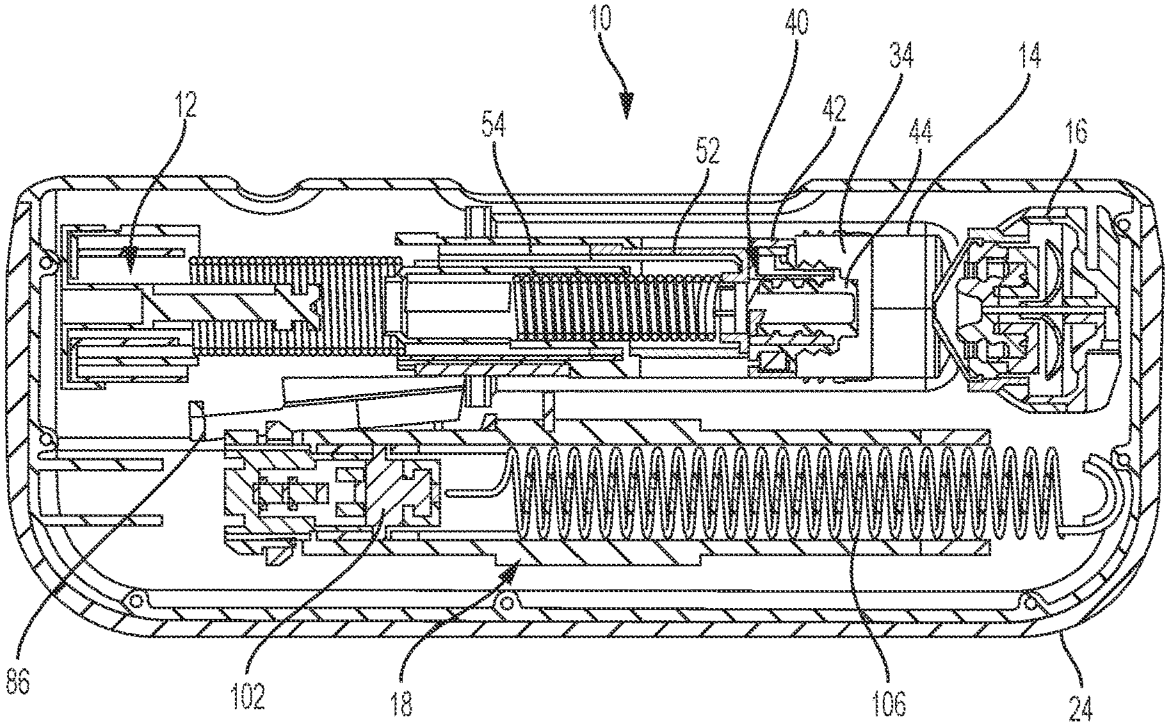
FIG. 11 is a top, cross-sectional view of the drug delivery system of FIG. 1 according to one aspect of the present invention, showing the drug delivery system in a use position.
Figure 12:
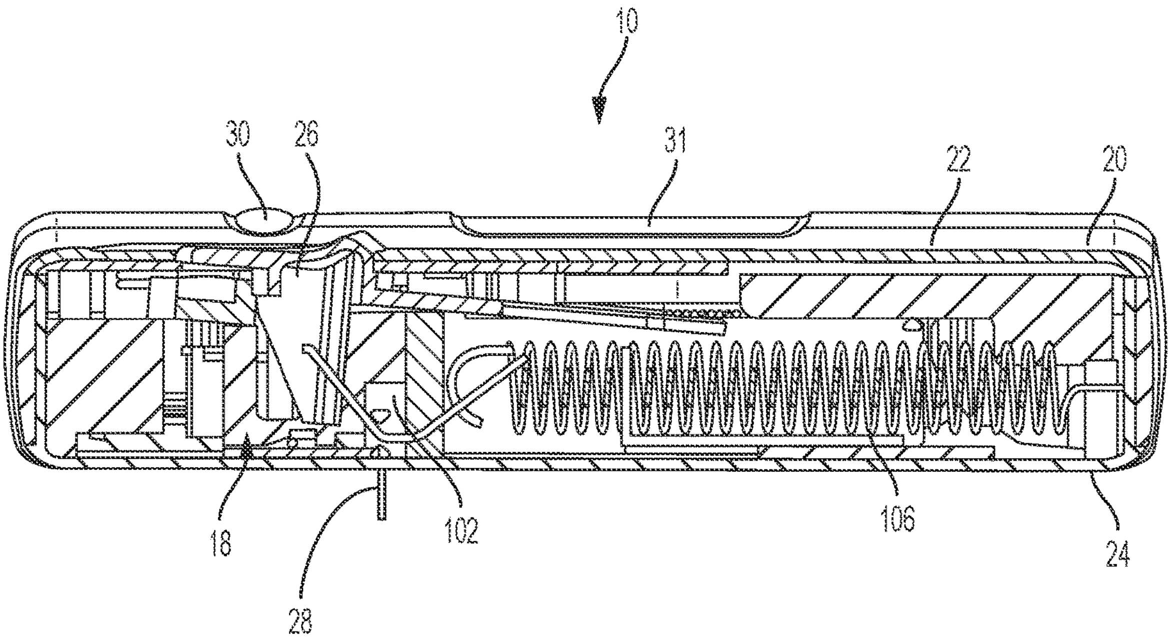
FIG. 12 is a front, cross-sectional view of the drug delivery system of FIG. 1 according to one aspect of the present invention, showing the drug delivery system in a use position.

During the use position of the system 10, as shown in FIGS. 10-12, the needle 28 is in the extended position at least partially outside of the housing 20 with the drive assembly 12 moving the stopper 34 within the container 14 to deliver the medicament from the container 14, through the needle 28, and to the user. In the use position, the valve assembly 16 has already pierced a closure 36 of the container 14 to place the container 14 in fluid communication with the needle 28, which also allows the drive assembly 12 to move the stopper 34 relative to the container 14 since fluid is able to be dispensed from the container 14. At the post-use position of the system 10, shown in FIGS. 13-15, the needle 28 is in the retracted position and engaged with a pad 38 to seal the needle 28 and prevent any residual flow of fluid or medicament from the container 14. The container 14 and valve assembly 16 may be the container 14 and valve assembly 16 shown and described in International Publication No. WO 2015/081337, which is hereby incorporated by reference in its entirety.

Figure 15:
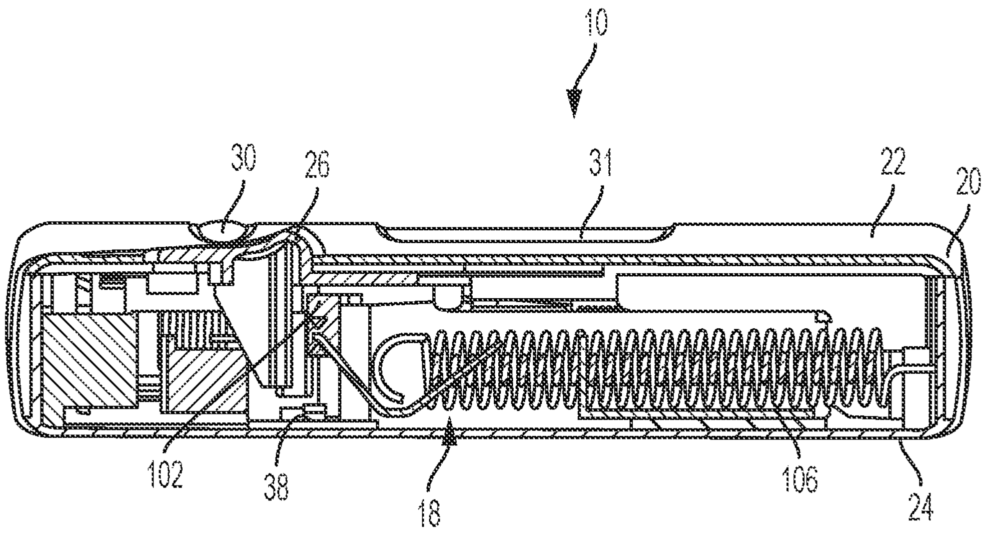
FIG. 15 is a front, cross-sectional view of the drug delivery system of FIG. 1 according to one aspect of the present invention, showing the drug delivery system in a post-use position.
Figure 16:
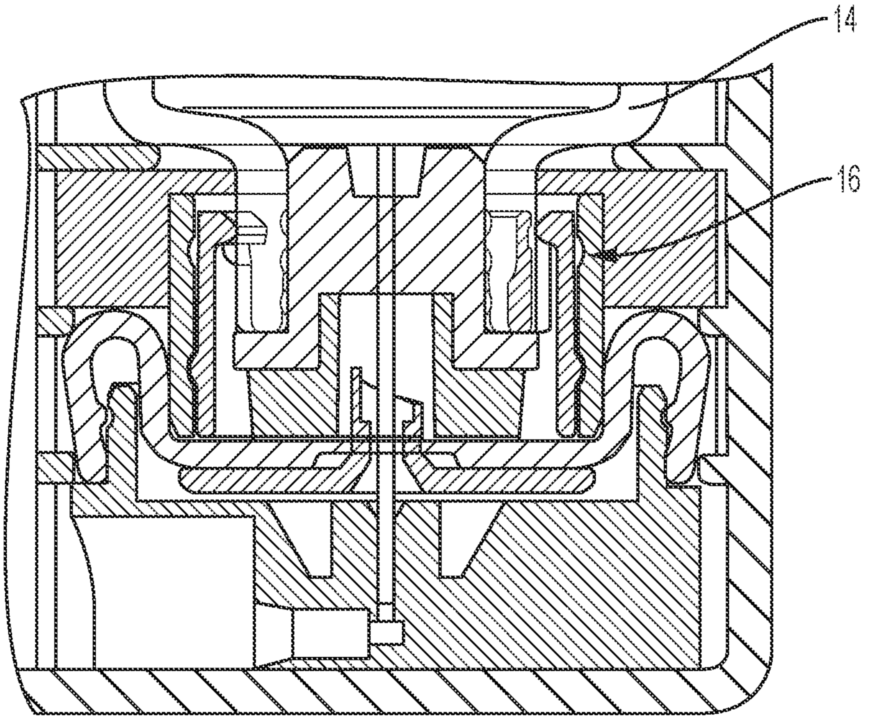
FIG. 16 is a partial cross-sectional view of the drug delivery system of FIG. 1 according to one aspect of the present invention, showing a valve assembly.
Figure 15A:
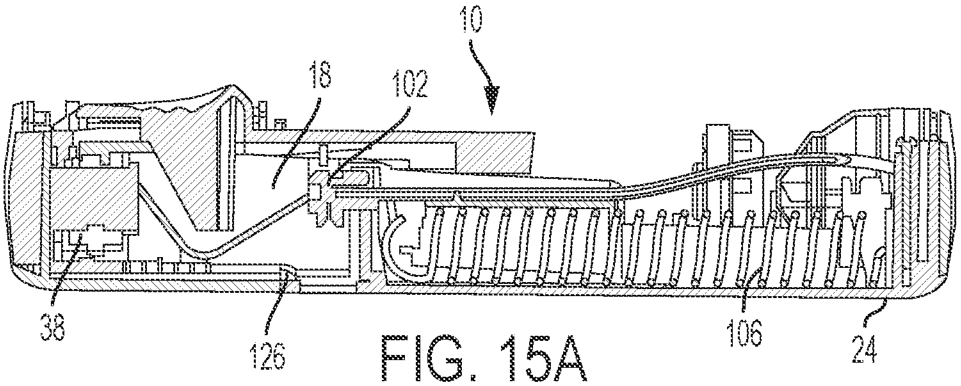
FIG. 15A is a front, cross-sectional view of the drug delivery system of FIG. 1 according to one aspect of the present invention, showing a pad with the drug delivery system in a pre-use position.
Figure 15B:
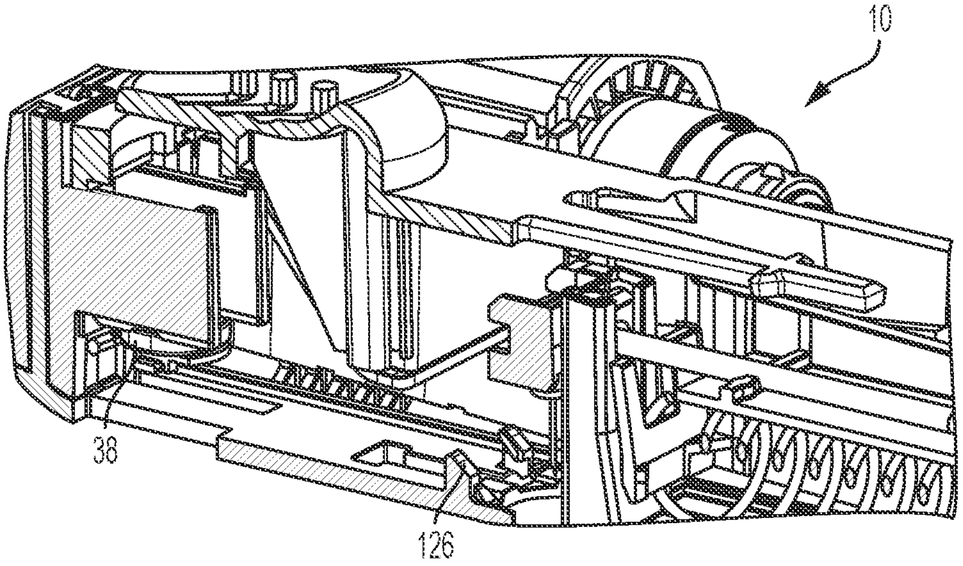
FIG. 15B is a perspective, cross-sectional view of the drug delivery system of FIG. 1 according to one aspect of the present invention, showing a pad with the drug delivery system in a pre-use position.
Figure 15C:
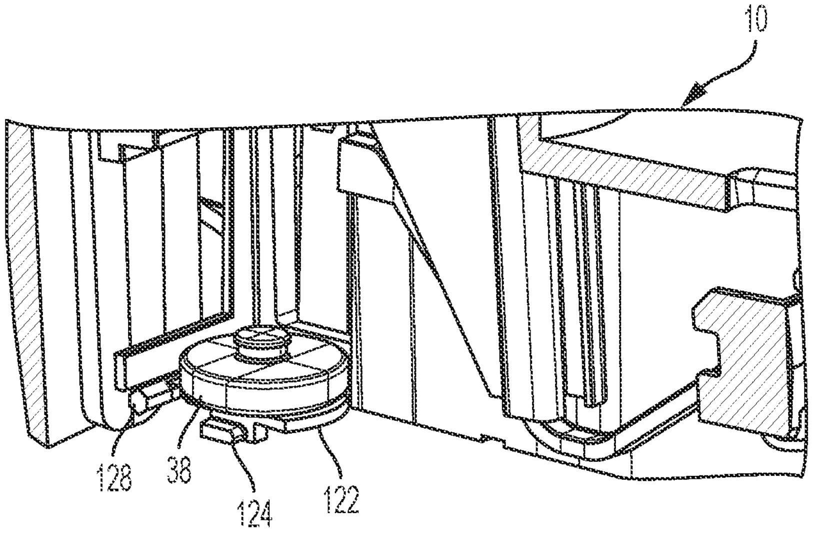
FIG. 15C is a perspective, cross-sectional view of the drug delivery system of FIG. 1 according to one aspect of the present invention, showing a pad with the drug delivery system in a pre-use position.

Referring to FIGS. 15A-15C, the pad 38 is biased into the pad as the needle actuator body 96 moves from the use position to the post-use position. In particular, the pad 38 is received by a pad arm 122 having a cam surface 124 that cooperates with a cam track 126 on the bottom portion 24 of the housing 20. The pad arm 122 is connected to the needle actuator body 96 via a torsion bar 128. The cam surface 124 is configured to engage the cam track 126 to deflect the pad arm 122 downwards thereby allowing the pad 38 to pass beneath the needle 28 before being biased upwards into the needle 28. The torsion bar 128 allows the pad arm 122 to twist about a pivot of the needle actuator body 96. The pad 38 may be press-fit into an opening of the pad arm 122, although other suitable arrangements for securing the pad 38 may be utilized.

Figure 13:
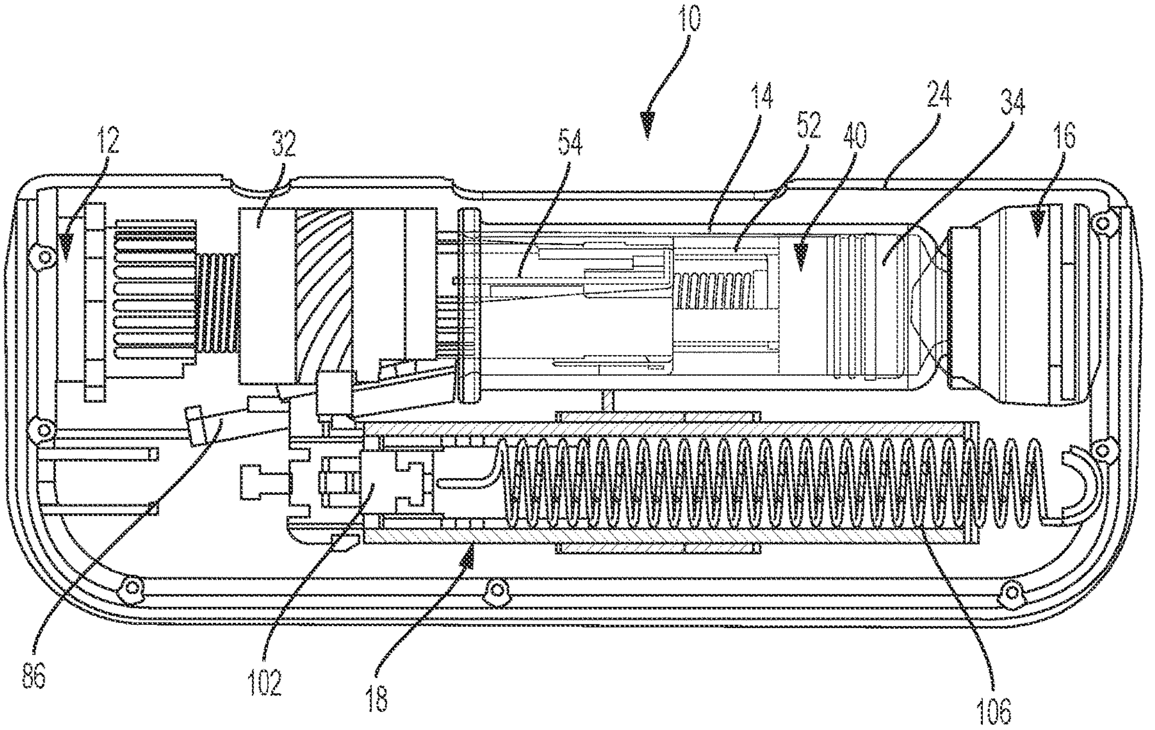
FIG. 13 is a top view of the drug delivery system of FIG. 1 according to one aspect of the present invention, showing a top portion of the housing removed and the drug delivery system in a post-use position.
Figure 14:
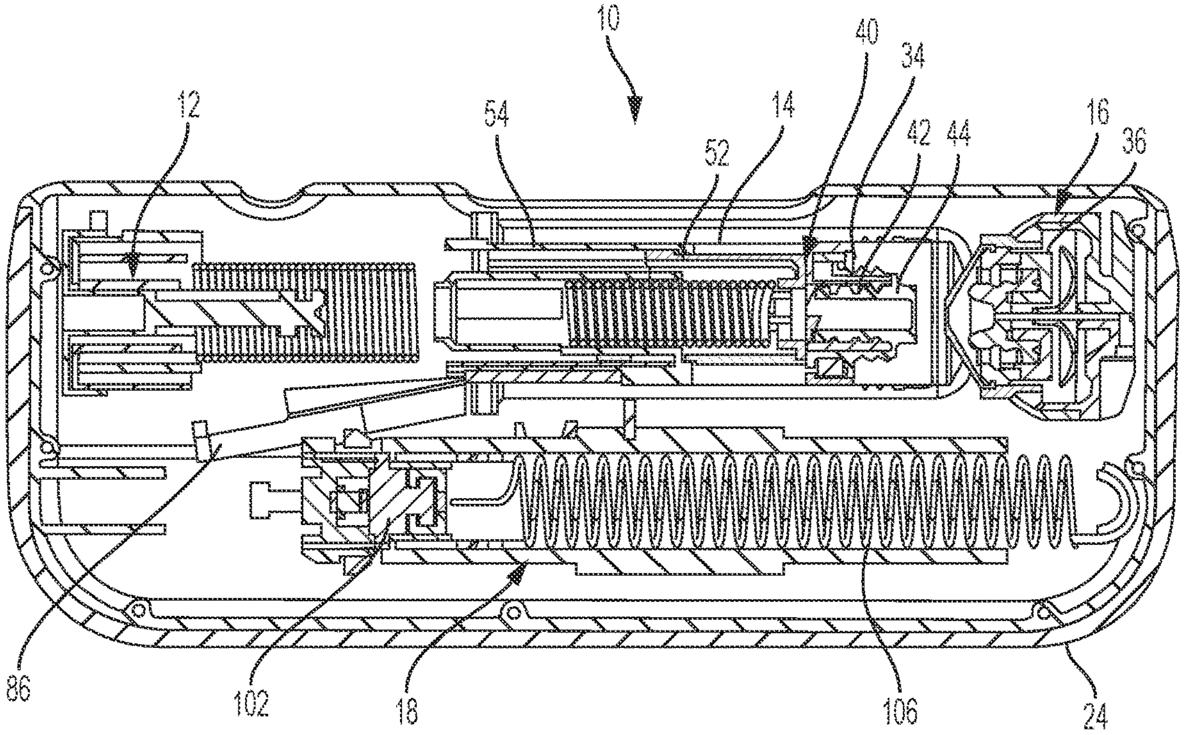
FIG. 14 is a top, cross-sectional view of the drug delivery system of FIG. 1 according to one aspect of the present invention, showing the drug delivery system in a post-use position.

Referring to FIGS. 1-16, the needle actuator assembly 18 according to one aspect of the present invention is shown. The needle actuator assembly 18 includes a needle actuator body 96 having guide surfaces 98, a needle shuttle 102 having cam surfaces (not shown), and the needle 28 received by the needle shuttle 102 and configured to be in fluid communication with the container 14 as discussed above. The needle actuator body 96 is generally rectangular with the guide surfaces 98 protruding radially inward. The needle shuttle 102 is received within the needle actuator body 96. As described above, the needle actuator body 96 is moveable within the housing 20 from a pre-use position (shown in FIGS. 4-6), an initial actuation position (FIGS. 7-9), a use position (FIGS. 10-12), and a post-use position (FIGS. 13-15). The needle actuator body 96 is biased from the pre-use position to the post-use position via an extension spring 106, although other suitable biasing arrangements may be utilized. The needle actuator body 96 is released and free to move from the pre-use position to the use position upon engagement of the actuator button 26, which is discussed in more detail below. The needle actuator body 96 moves from the use position to the post-use position after rotation of the restriction member 86.

Figure 17:
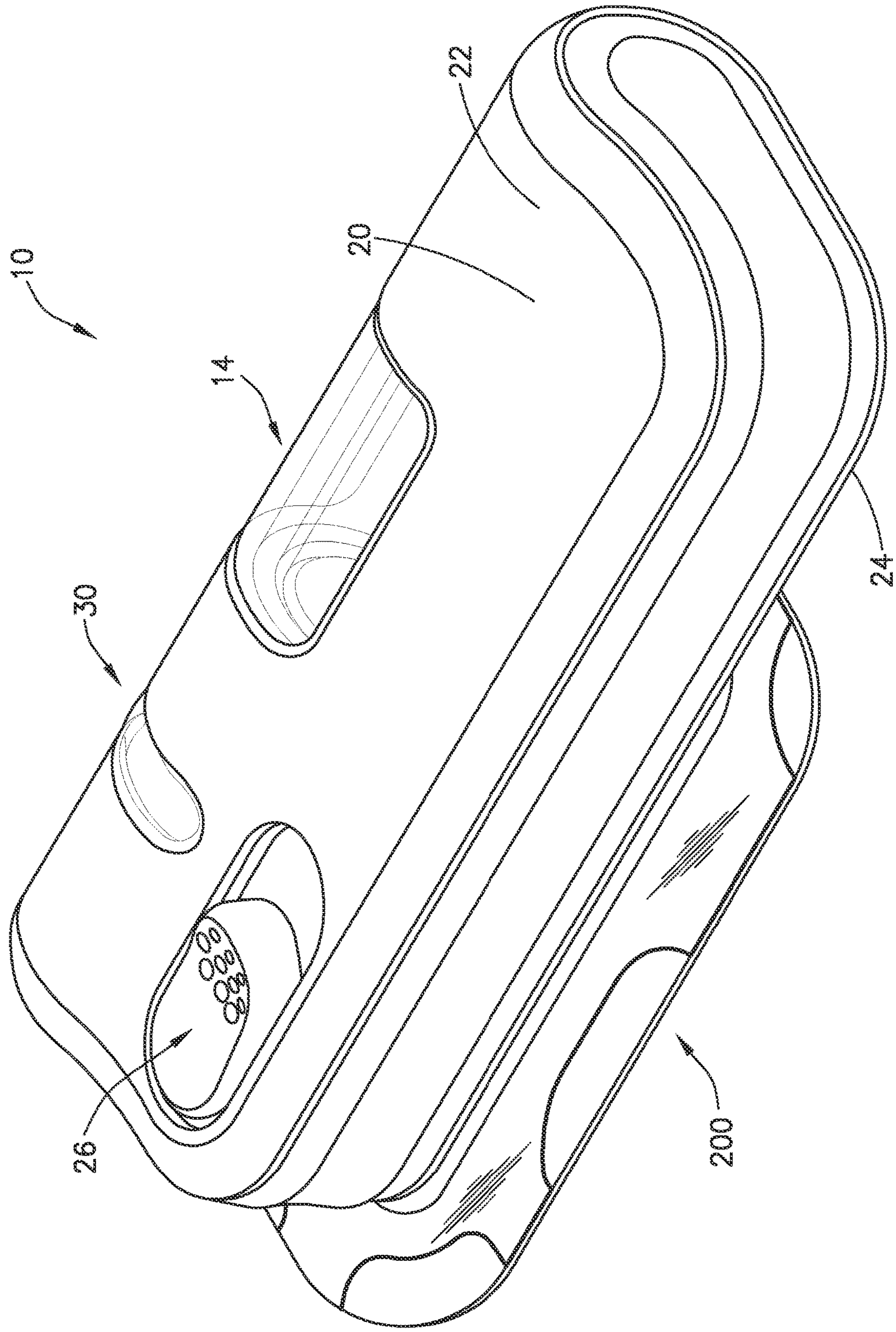
FIG. 17 is a top perspective view of an integrated adhesive liner and needle shield remover in accordance with an aspect of the present disclosure.
Figure 18:
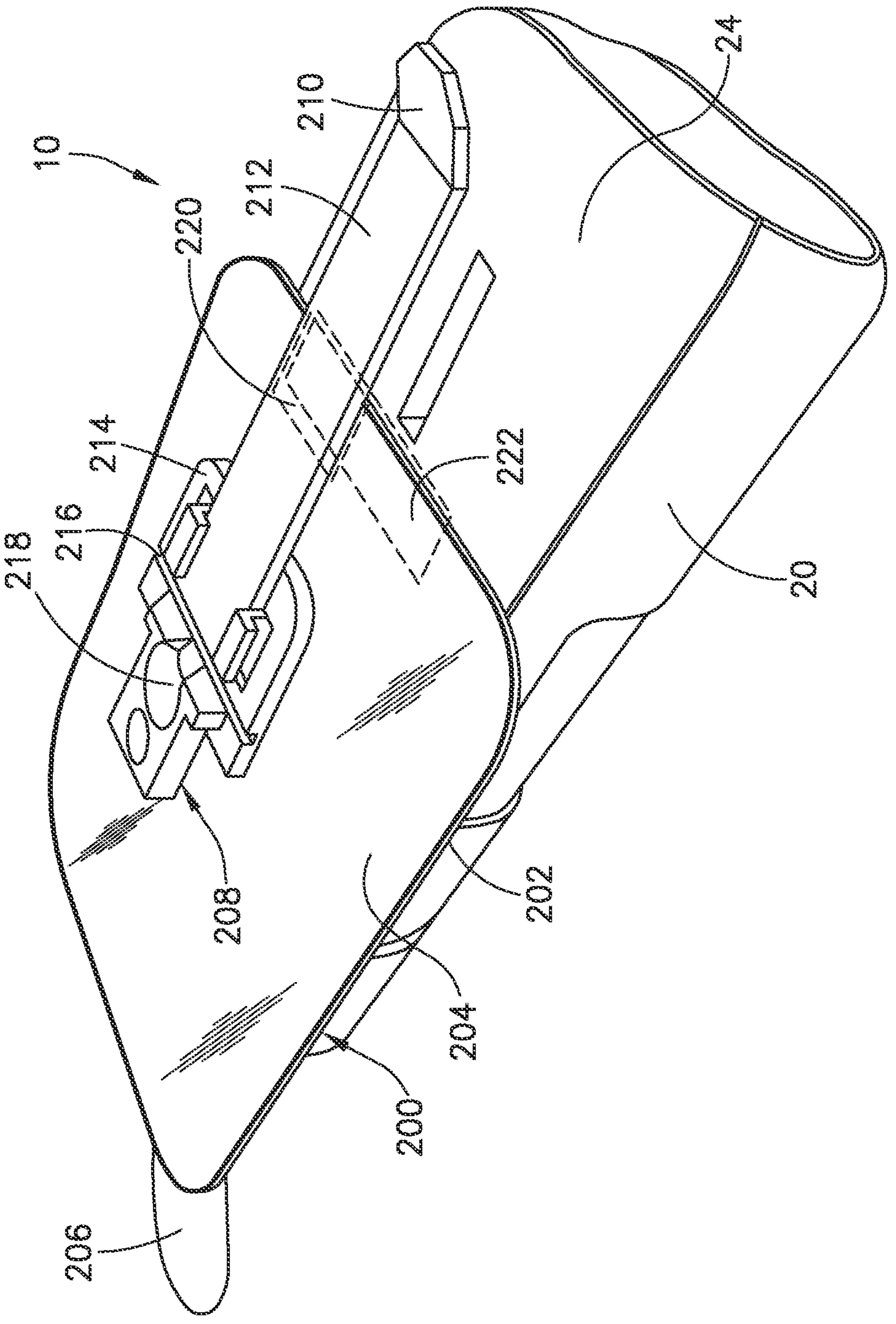
FIG. 18 is a bottom perspective view of the integrated adhesive liner and needle shield remover of FIG. 17 in a first position.

Next, referring to FIGS. 17 and 18, the system 10 in accordance with another aspect of the present disclosure is illustrated. Specifically, system 10 shown in FIGS. 17 and 18 includes an adhesive pad element 200 at least partially affixed to the bottom portion 24 of housing 20. The adhesive pad element 200 may be affixed to the bottom portion 24 by any appropriate means, such as, e.g., a mechanical coupling, an adhesive coupling, etc. Adhesive pad element 200 may be formed of any suitable flexible material such as, e.g., foam, rubber, plastic, fabric, etc. A patient-facing side of the adhesive pad element 200 (i.e., the side facing away from bottom portion 24) is configured to include an adhesive surface, which enables the system 10 to be selectively adhered to the patient's skin prior to an injection procedure. In some embodiments, a peripheral portion of adhesive pad element 200 may extend beyond the footprint of housing 20, thereby providing for an increased surface area and improved adhesive contact between the adhesive pad element 200 and the patient's skin. Furthermore, due to the flexible nature of the adhesive pad element 200, the adhesive pad element 200 may substantially conform to the contours of the patient's skin surface upon which the system 10 is attached.

FIG. 18 illustrates a bottom perspective view of system 10, including adhesive pad element 200. In a pre-use configuration, adhesive pad element 200 includes at least two layers, a primary adhesive layer 202, and a removable liner 204. The patient-facing surface of primary adhesive layer 202 is an adhesive surface, while the liner 204 is configured to cover the primary adhesive layer 202 prior to use. The liner 204 is configured to be fully removable (i.e., peelable) from the primary adhesive layer 202 so as to expose the adhesive surface of primary adhesive layer 202 only shortly before attachment of system 10 onto the patient's skin surface. As part of the adhesive pad element 200, both the primary adhesive layer 202 and the liner 204 may be formed of any appropriate flexible material such as, e.g., foam, rubber, plastic, fabric, etc., and may be formed of the same or different materials.

Adhesive pad element 200 may also include an injector removal tab 206. The injector removal tab 206 may be formed as part of, or be coupled to, the primary adhesive layer 202 of adhesive pad element 200. In the embodiment shown in FIG. 18, the injector removal tab 206 extends from a single corner of the adhesive pad element 200. However, it is to be understood that injector removal tab 206 may extend from any corner or edge of the adhesive pad element 200, and more than one injector removal tab 206 may be utilized. The injector removal tab 206 includes two non-adhesive surfaces, and is sized to be graspable by a patient or user. After an injection procedure is completed and the needle of system 10 is automatically removed the patient's skin, the patient or other user may grasp and pull the injector removal tab 206 to peel the adhesive pad element 200 away from the skin surface, thereby removing the system 10 from contact with the skin surface.

Referring still to FIG. 18, system 10 further includes a needle shield remover 208. The needle shield remover 208 is positioned over the adhesive pad element 200 at a substantially centralized location, with a shield portion 218 of the needle shield remover 208 passing through the liner 204 and the primary adhesive layer 202 of the adhesive pad element 200, as well as through an opening (not shown) in the bottom portion 24 of the housing 20. The shield portion 218 forms a needle shield portion on an end thereof, which is configured to provide protection over the needle 28 of the needle assembly 18 of the system 10 prior to use (i.e., in the configuration shown in FIG. 6). Furthermore, the shield portion 218 may also be configured to prevent inadvertent initiation of the injection process, with removal of the needle shield remover 208 necessitated to initiate the injection process.

The needle shield remover 208 further includes a grasping portion 210, an elongated arm 212, a base portion 214, and a hinge portion 216. As shown in FIG. 18, in a first (or non-use) position, the elongated arm 212 extends along the bottom portion 24 of housing 20 in a direction opposite that of the adhesive pad element 200, laying substantially flat along the bottom portion 24. Additionally, the grasping portion 210 may be located on a distal end of elongated arm 212, and may angle upwardly away from the bottom portion 24 of housing 20 so as provide a gripping surface for the user in the form of, e.g., a pull tab. However, it is to be understood that the needle shield remover 208 is not limited to such a grasping portion and/or elongated arm, and may utilize any appropriate means of removal of the needle shield remover.

The base portion 214 may be coupled to the liner 204 of the adhesive pad element 200 via any suitable method such as, e.g., an adhesive, a mechanical connection, etc. The hinge portion 216 located substantially on or adjacent to the base portion 214 enables the elongated arm 212 to at least partially pivot relative to the bottom portion 24. When the user wishes to remove the needle shield portion (not shown) protecting the needle 28, the user pivots the elongated arm 212 by way of the grasping portion 210 from a first position substantially flat along the bottom portion 24 to a second position angled away from the bottom portion 24 (e.g., substantially perpendicular to the bottom portion 24). From the second position, the needle shield remover 208 may be pulled in a direction substantially normal to the bottom portion 24 of housing 20 so as to disengage the needle shield (and needle shield remover 208) from the system 10.

Additionally, and in accordance with an aspect of the present disclosure, movement of the elongated arm 212 of needle shield remover 208 from the first position to the second position also acts to initiate removal of the liner 204 from the primary adhesive layer 202, thereby providing for removal of the needle shield remover 208 and the liner 204 in a single user step. As is shown in FIG. 18, an underside portion 220 of the elongated arm 212 may be affixed to a top surface of the liner 204 via, e.g., an adhesive or mechanical connection. The underside portion 220 is located proximate to a front edge portion 222 of the adhesive pad element 200. The front edge portion 222 is itself adhered to the bottom portion 24 of the housing 20. Thus, at the front edge portion 222, the primary adhesive layer 202 of the adhesive pad element 200 is held in contact with the bottom portion 24 at all times, regardless of the pulling force on liner 204.

Figure 21:
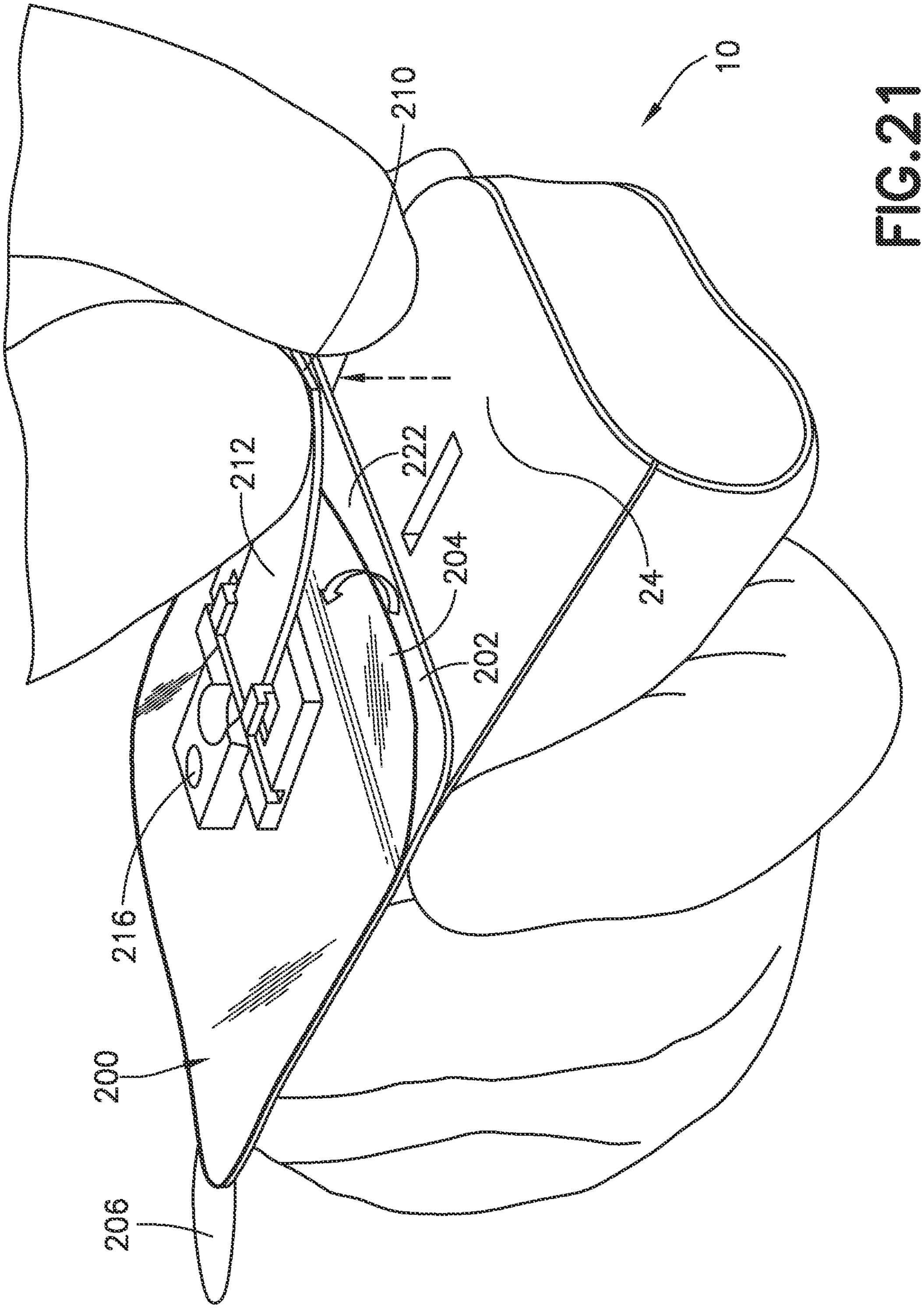
FIG. 21 is a bottom perspective view of the integrated adhesive liner and needle shield remover of FIG. 18 in a second position.

Referring to FIGS. 18 and 21, when the user pivots the elongated arm 212 about the hinge portion 216 in order to remove the needle shield from the system 10, the adhered underside portion 220 of the elongated arm 212 peels the liner 204 away from primary adhesive layer 202, with the peeling process beginning at or near the front edge portion 222 of the adhesive pad element 200. As the user continues to pivot the elongated arm 212 in order to ultimately remove the needle shield remover 208 from the system 10, the liner 204 concurrently peels away from the primary adhesive layer 202 until it is entirely removed along with the needle shield remover 208. As the peeling process of the liner 204 begins at the front edge portion 222 of the adhesive pad element 200, the peeling of liner 204 is far more intuitive to the user than prior art configurations, and also eliminates the need for complex cuts or perforations to be made in only on the liner in order to accommodate "inside-out" peeling of the liner, as is done in prior art configurations. Furthermore, as the front edge portion 222 is also adhered to the bottom portion 24 of the housing 20, the peeling action via the elongated arm 212 is unlikely to cause tears or other damage to the adhesive pad element 200.

While needle shield remover 208 is shown in FIGS. 18 and 21 to include a hinge portion 216, in some embodiments, it is to be understood that hinge portion 216 could be eliminated. In such configurations, only the component material flexibility of the elongated arm 212 would be needed to both peel the liner 204 from the primary adhesive layer 202 and initiate removal of the needle shield remover 208 from the system 10.

Figure 19:
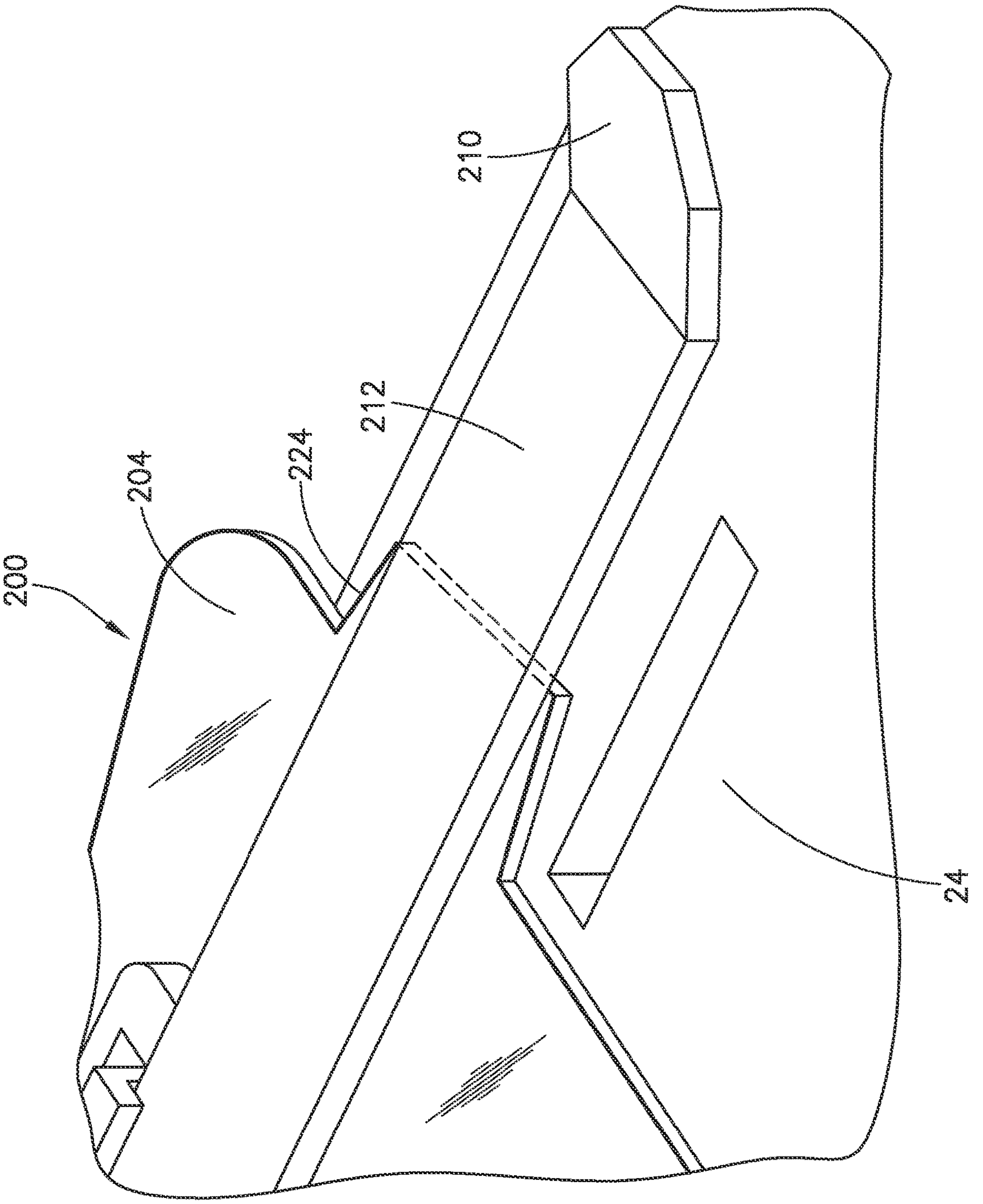
FIG. 19 is a partial bottom perspective view of an integrated adhesive liner and needle shield remover in accordance with another aspect of the present disclosure.

Next, referring to FIG. 19, and in accordance with another aspect of the present disclosure, the adhesive pad element 200 may further include an extended portion 224. The extended portion 224 may be configured to extend only below the elongated arm 212, with a top surface of the extended portion 224 being adhered to the underside of the elongated arm 212 via, e.g., an adhesive or mechanical connection. With such a configuration, the initial peel force on the liner 204 when the elongated arm 212 is pivoted may be reduced, thereby simplifying removal of the liner 204 from the primary adhesive layer 202 and reducing the likelihood of tearing or damage to the adhesive pad element 200.

Figure 20:
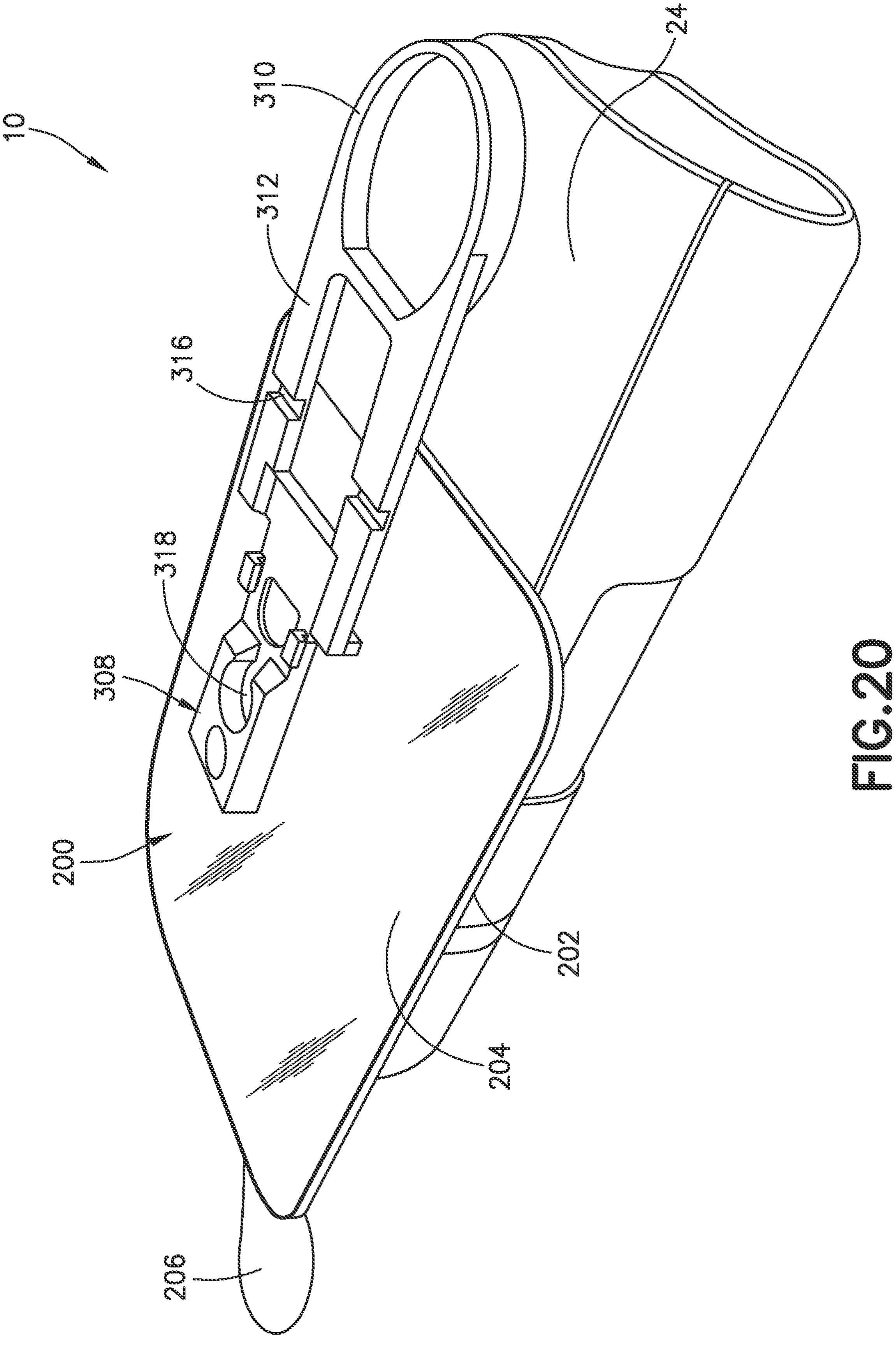
FIG. 20 is a bottom perspective view of an integrated adhesive liner and needle shield remover in accordance with another aspect of the present disclosure.

Referring now to FIG. 20, a needle shield remover 308 in accordance with another aspect of the present disclosure is shown. While the needle shield remover 208 described above with respect to FIGS. 18 and 21 utilized an elongated arm 212 and grasping portion 210 in the form of, e.g., a pull tab, the needle shield remover 308 shown in FIG. 20 includes a pull ring 310 coupled to an extended portion 312, with the extended portion 312 being pivotable about a hinge 316. The needle shield remover 308 also includes a shield portion 318 passing through the liner 204 and the primary adhesive layer 202 of the adhesive pad element 200, as well as through an opening (not shown) in the bottom portion 24 of the housing 20. The shield portion 318 forms a needle shield on an end thereof, which is configured to provide protection over the needle 28 of the needle assembly 18 of the system 10 prior to use (i.e., in the configuration shown in FIG. 6). Furthermore, the shield portion 318 may also be configured to prevent inadvertent initiation of the injection process, with removal of the needle shield remover 308 necessitated to initiate the injection process.

While not shown in FIG. 20, it is to be understood that an underside of extended portion 312 which contacts the top surface of liner 204 is adhered to the liner 204 in this location via, e.g., an adhesive or mechanical connection. Thus, when the user wishes to remove the needle shield remover 308 from the system 10, the user grasps the pull ring 310 and pivots the pull ring 310 from a first position to a second position, with the second position being substantially normal to the bottom portion 24. Then, pulling in a direction substantially normal to the bottom portion 24, the liner 204 is peeled from the primary adhesive layer 202 concurrently with removal of the needle shield remover 308. As the connection between the needle shield remover 308 and the liner 204 is initially provided at the underside of the extended portion 312, this pulling force causes the liner 204 to be peeled from an edge portion of the adhesive pad element 200, which eliminates the need for complex cuts or perforations to be made in only on the liner in order to accommodate "inside-out" peeling of the liner, as is done in prior art configurations.

Elements of one disclosed aspect can be combined with elements of one or more other disclosed aspects to form different combinations, all of which are considered to be within the scope of the present invention.

While this disclosure has been described as having exemplary designs, the present disclosure can be further modified within the spirit and scope of this disclosure. This application is therefore intended to cover any variations, uses, or adaptations of the disclosure using its general principles.

Further, this application is intended to cover such departures from the present disclosure as come within known or customary practice in the art to which this disclosure pertains and which fall within the limits of the appended claims.

What is claimed is:

1. A drug delivery system comprising: a housing having a top portion and a bottom portion; a needle having a retracted position within the housing and an extended position outside of the housing; an adhesive pad element coupled to the bottom portion of the housing, wherein the adhesive pad element comprises a primary adhesive layer and a removable liner; a needle shield portion configured to at least partial cover the needle in the retracted position; and a needle shield remover coupled to the needle shield portion, wherein the needle shield remover comprises a base member coupled to the removable liner, an elongated member separate from the removable liner and configured to extend along the bottom portion of the housing in a first position and extend away from the bottom portion of the housing in a second position, a grasping portion on a distal end of the elongated member, and a hinge substantially on or adjacent to the base portion that enables the elongated member to pivot from the first position to the second position, with a bottom surface portion of the elongated member being coupled to the removable liner at only a location that is proximate to a front edge location of the adhesive pad element such that the removable liner is peeled away from the primary adhesive layer when the elongated member of the needle shield remover is moved from the first position to the second position, with the removable liner being peeled away from the primary adhesive layer in a single direction from the front edge location of the adhesive pad toward an opposing back edge location of the adhesive pad.

2. The drug delivery system of claim 1, wherein the grasping portion comprises a pull tab.

3. The drug delivery system of claim 2, wherein the pull tab is angled upwards relative to the bottom portion of the housing when the elongated member is in the first position.

4. The drug delivery system of claim 1, wherein the grasping portion comprises a pull ring.

5. The drug delivery system of claim 1, wherein the bottom surface portion of the elongated member is coupled to the removable liner by an adhesive.

6. The drug delivery system of claim 1, wherein the adhesive pad element further comprises an extended portion extending below the bottom surface portion of the elongated member.

7. The drug delivery system of claim 1, wherein a shielding portion of the needle shield remover passes through the liner of the adhesive pad element, the primary adhesive layer of the adhesive pad element, and an opening formed in the housing to allow the needle to extend therethrough in the extended position.

8. The drug delivery system of claim 1, wherein the adhesive pad element further comprises an injector removal tab.

9. The drug delivery system of claim 1, wherein a peripheral portion of the adhesive pad element extends beyond a footprint of the housing.

10. The drug delivery system of claim 1, wherein the adhesive pad element is formed of one or more flexible materials.

11. The drug delivery system of claim 1, wherein the elongated member of the needle shield remover is formed of a flexible material.

12. The drug delivery system of claim 1, wherein the elongated member of the needle shield remover lays substantially flat along the bottom portion of the housing when in the first position.

13. A method of preparing a wearable drug delivery system for use, the method comprising:

providing a drug delivery system comprising:

a housing having a top portion and a bottom portion;

a needle having a retracted position within the housing and an extended position outside of the housing;

an adhesive pad element coupled to the bottom portion of the housing, wherein the adhesive pad element comprises a primary adhesive layer and a removable liner;

a needle shield portion configured to at least partial cover the needle in the retracted position; and a needle shield remover coupled to the needle shield portion, wherein the needle shield remover comprises a base member coupled to the removable liner, an elongated member separate from the removable liner and having a grasping portion on a distal end thereof, the elongated member configured to extend along the bottom portion of the housing in a first position and extend away from the bottom portion of the housing in a second position, a grasping portion on a distal end of the elongated member, and a hinge substantially on or adjacent to the base portion that enables the elongated member to pivot from the first position to the second position, with a bottom surface portion of the elongated member being coupled to the removable liner proximate to an edge location of the adhesive pad element, with the removable liner being peeled away from the primary adhesive layer in a single direction from the front edge location of the adhesive pad toward an opposing back edge location of the adhesive pad;

pivoting the elongated member about the hinge portion from the first position towards the second position such that the removable liner is peeled away from the primary adhesive layer at the edge location of the adhesive pad element; and pulling the grasping portion of the needle shield remover to both remove the needle shield portion from the housing and remove the removable liner from the primary adhesive layer.

14. The method of claim 13, wherein the grasping portion of the needle shield remover comprises a pull ring.

15. The method of claim 13, wherein the edge location of the adhesive pad element is a front edge portion coupled to the bottom portion of the housing via an adhesive, and further wherein the bottom surface portion of the elongated member is coupled to the removable liner of the adhesive pad element at a location proximate to the front edge portion.

* * * * *